United States Patent [19]

Marchello

[11] 4,273,119

[45] Jun. 16, 1981

[54] BREATHING MASK FOR HORSES

[76] Inventor: John L. Marchello, 57751 Grand River Ave., New Hudson, Mich. 48165

[21] Appl. No.: 124,801

[22] Filed: Feb. 26, 1980

[51] Int. Cl.[3] .................... A61M 15/00; A62B 23/06; B68B 5/00

[52] U.S. Cl. .................... 128/201.13; 54/80; 119/129

[58] Field of Search .................... 119/129, 130, 133; 128/201.13; 54/80

[56] References Cited

U.S. PATENT DOCUMENTS

| | | | |
|---|---|---|---|
| 432,317 | 7/1890 | Lowe | 119/133 |
| 1,516,202 | 11/1924 | Nelson | 54/80 |
| 3,491,755 | 1/1970 | Barghini et al. | 54/80 X |
| 3,609,941 | 10/1971 | Eldredge | 54/80 |
| 4,141,199 | 2/1979 | Doino, Jr. | 119/129 X |

*Primary Examiner*—Hugh R. Chamblee
*Attorney, Agent, or Firm*—Cullen, Sloman, Cantor, Grauer, Scott & Rutherford

[57] ABSTRACT

A feed bag-like breathing mask for fitting over the forward end of a horse's head, comprises a frame and a bag-like cover carried upon and shaped to closely fit over the frame. The frame is formed of semi-flexible, flat strips providing a rear opening base band for encircling the horse's head rearwardly of the mouth and nostrils, and longitudinal frame strips extending from the base band and joined together at their forward ends. The strips are bent to form an approximately dome-like shape for completely receiving, but being spaced outwardly away from, the forward portion of the horse's head. The cover is formed of a relatively thick, open cell, foamed plastic material. The cells are of a size to substantially freely pass air but to screen a substantial portion of the dust and dirt carried by the air. The cover is sufficiently thick to tend to produce a cold weather breathing cycle wherein some of the moisture in exhaled breath condenses within the cover material, near the inner surface of the cover, to thereby tend to insulate and retain some heat within the mask, and upon exhaling, the incoming dry, fresh air tends to pick up some of the condensed moisture and is somewhat preheated before inhaling.

6 Claims, 10 Drawing Figures

BREATHING MASK FOR HORSES

BACKGROUND OF INVENTION

Various types of breathing masks have been used for race horses for the general purpose of filtering out dust and dirt during training on dustytracks, and also to protect the horse during cold weather training. An example of a prior type of breathing mask is described in the Equine Veterinary Journal, Volume 5, No. 3, issue of July 1973, on pages 131 through 134. This article describes some of the investigation work done in connection with the masks for use in below freezing temperatures. It also illustrates and describes a prior art mask which was marketed at one time, but apparently was not satisfactory and was withdrawn from the market.

In general, prior masks have been unsuccessful or have been difficult to use and have not provided adequate protection to the horse. Thus, there has been a need for an effective breathing mask, particularly for training race horses, which is simple to use, relatively inexpensive, and protects the horse against the various track and weather problems encountered.

Among the problems encountered is that in many areas, during certain times of the year, the tracks are dusty or dirty so that an additional burden of excess dust is placed upon the horse's nasal passages. Such excess dust tends to act to dry the nasal passages, thereby interferring with the function of the nasal passages which has to do with filtering dust and air borne germs and pre-warming the air entering the horse's body. It is believed that continual exposure to excess dust or dirty breathing conditions, particularly in young race horses, will produce chronic breathing difficulties. Hence, a suitable mask which serves to filter a substantial portion of the excess dust or dirt is desirable, provided it does not otherwise interfere with the horse's breathing.

Another problem encountered, particularly during training, is that in below freezing temperatures, various respiratory difficulties tend to develop as a result of the heavy intake of cold air, and particularly dry cold air, which affects the horse's breathing patterns and the nasal cavities.

Another problem which commonly arises in training race horses is that from time to time it is necessary to provide the horse with vaporizer-types of medication, particularly in aiding congestion problems and cleansing the horse's nasal passages. Thus, a suitable holder or container or mask which can be used for vaporizing inhalants, as a substitute for electric vaporizers or sealed room "steaming," is desirable.

Thus, the invention herein relates to a breathing mask construction which is particularly useful in handling the foregoing problems encountered in training or in otherwise handling horses.

SUMMARY OF INVENTION

The invention herein contemplates an improved breathing mask for fitting over and being secured upon the forward end of a horse's head, including the nostril, nose and mouth portions thereof. In general, the mask comprises a frame, which is approximately dome-shaped for fitting over the forward end of the horse's head, but is spaced outwardly of the surrounded nose portion of the horse's head. A thick cover, shaped like the frame, is mounted upon and carried by the frame. The cover is formed of an open cell, foamed plastic material which tends to freely pass air. However, the cell sizes are sufficient to tend to filter or catch much of the dirt or dust which might otherwise pass directly to the horse during breathing. In addition, the wall thickness of the cover is selected so that during cold weather breathing cycles, there is a tendency for some moisture of exhaled breath to condense within the wall of the cover, near the inner surface thereof. This condensation serves like an insulator to hold some heat within the mask between the frame and the horse's face. Upon inhaling, the fresh air passes through the cover and tends to pick up moisture, particularly when the air is dry, and to be pre-warmed to some extent, before being inhaled.

The mask is designed to remain firmly in place upon the horse's head, during heavy exercise as well as during the times that the horse is stationary. For such positioning, the frame is formed with a padded band which surrounds the rearward opening of the mask and rests upon the encircled portion of the horse's head. In addition, an inner nose bar is secured to the band, and extends inwardly through the mask to the closed end thereof. The bar is located so as to be positioned upon and between the horse's nostrils, thereby positioning the mask at a distance from the face. Suitable strap means pass around the horse's head and hold the bag-like mask in position, almost in the same manner as a nose feed bag.

One of the objects of the invention is to so form the mask that it can be easily and simply cleaned and also that it is durable and resists breakage. This is accomplished by forming the frame out of a semi-resilient, i.e. a relatively stiff, self sustaining, flat plastic stripping, which can be flexed upon suitable manual force, but tends to return to its pre-location. Thus, bending or distortion or movement of the mask due to impact against surrounding objects, such as the wall of a paddock, or the like, results in the mask flexing, rather than breaking, and then returning to its pre-determined shape.

Further, the mask cover is provided with an outer net covering which maintains the shape thereof and prevents excess deterioration. Consequently, the mask may be cleaned, relatively easily, by hosing it on its inside, with water.

Another object of the invention is to provide a mask construction which can be utilized without difficulty as an inhaler device, by placing an inhalent material within the mask which can be breathed by the horse during normal breathing through the mask.

Another object of the invention is to provide a relatively inexpensive mask construction which can be used for a considerable period of time, during year round conditions where either excess dust or dirt is encountered upon the training track or during cold weather use to protect the horse while minimally interfering with normal breathing.

These and other objects and advantages of this invention, will become apparent, upon reading the following decription, of which the attached drawings form a part.

DETAILED DESCRIPTION

Figure 1:
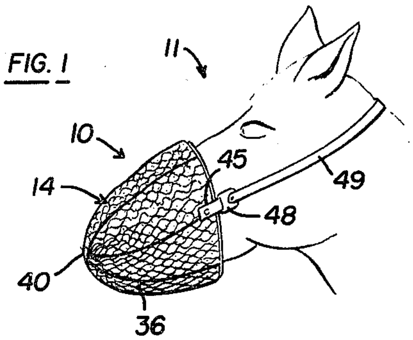
FIG. 1 shows the mask fastened in place upon the forward or nose end of a horse's head.
Figure 2:
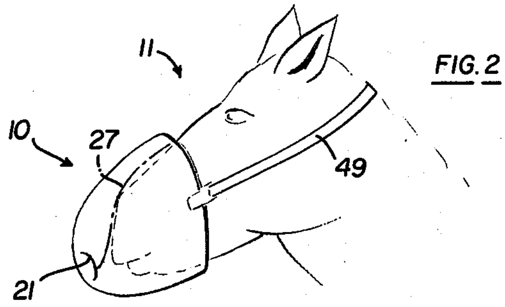
FIG. 2 is a schematic view, similar to FIG. 1, showing the position of the horse's nose relative to the mask.
Figure 3:
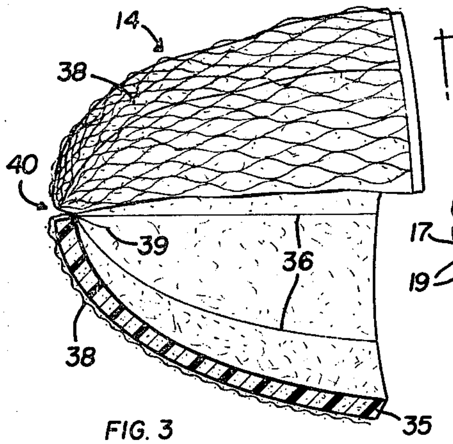
FIG. 3 is an enlarged, partly in cross section, elevational view of the mask cover.

FIGS. 1 and 2 illustrate the breathing mask 10 mounted upon the forward or nose end of the head 11 of a horse.

Figure 4:
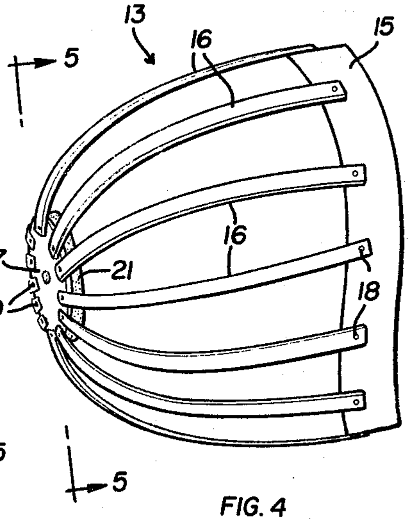
FIG. 4 is an elevational view of the mask frame.
Figure 5:
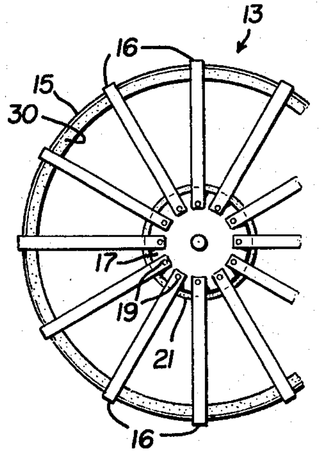
FIG. 5 is a forward end view of the mask frame taken in the direction of arrows 5—5 of FIG. 4.
Figure 6:
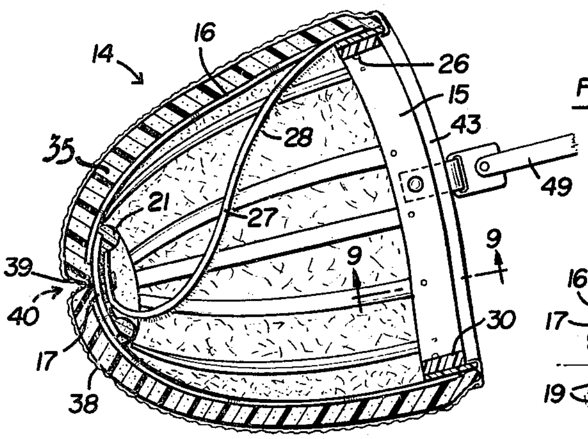
FIG. 6 is a cross-sectional view of the mask assembly.
Figure 7:
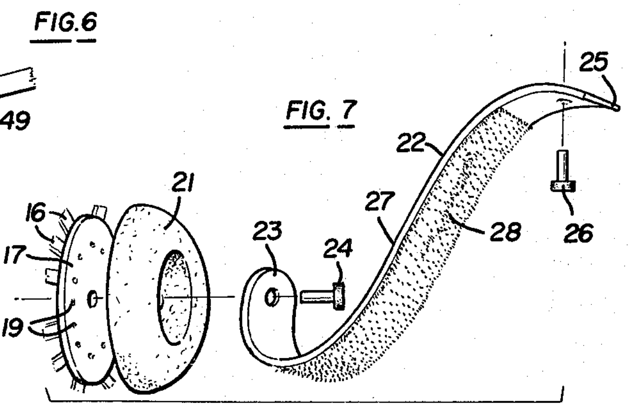
FIG. 7 is a fragmentary, perspective view, of several elements of the frame.

The mask is composed of a frame 13 and a cover 14. The frame, as illustrated in FIGS. 4, 5 and 6, includes a flat, thin, semi-flexible, relatively stiff, but resilient strip or band 15 for encircling the lower portion of a horse's head. A number of thin strips 16, preferably made of the same material as the band 15, extend lengthwise of the horse's head from the band to the crown or closed end of the dome-like shaped frame. A flat disk 17 closes the forward end of the dome.

The rear ends of strips 16 are secured to the band by means of suitable rivets 18. The forward ends of the strips are fastened to the disk 17 by means of rivets 19. Between the opposite ends, the strips are bent to provide the dome-like shape, which is somewhat similar to the feed-bag shape used in feeding horses.

The material used for the strips may vary, but it is intended that the material is normally stiff or self-sustaining in shape, yet may be flexed and resiliently returned to shape. Hence, the application of sufficient force, such as manual force or pressure due to the horse pressing the mask against a surrounding obstacle such as a wall or post or the like, will momentarily distort and bend or flex the frame. However, the frame will return to normal shape upon release of the pressure. Useful plastic materials for this purpose are commercially available, high density polyethylene sheets of about one-sixteenth of an inch in thickness. Other useful plastics are high density polypropylene, semi-rigid vinyl, medium density urethane or the like. The particular plastic selected is not significant to the invention hereof, so long as it provides the described function. Normally, the manufacturer of this product will select the best commercially available plastic which is available at the lowest price for this purpose.

A thick, foam plastic pad 21, made of a suitably resilient foam plastic material which is liquid absorbent, is positioned on the inner surface of the disk 17. Further, a nose bar 22, made of a plastic strip, similar to the frame strips described above, is arranged within the frame. The forward end of the nose bar is bent to form a bent end 23 which is secured by a river 24 through the pad 21 and the disk 17.

The opposite end of the nose bar is bent at 25 and is riveted to the band 15 by rivet 26 (see FIG. 6). The middle portion 27 of the nose bar is bent around to rest upon the upper surface of the nose portion of the horse, between the nostrils, for thereby supporting, centering and holding the mask upon the horse's head. For comfort purposes, a foam plastic padding strip 28 is adhesively secured to the inner surface of the middle portion of the nose bar.

As illustrated schematically in FIG. 2, the nose bar causes the mask to remain spaced away from the horse's nostrils, thereby providing a preheat space within the interior of the mask and in front of the horse's nostrils.

A relatively thick, resilient foam plastic pad strip 30 is adhesively secured to the inner face of the band 15. Thus, the band comfortably encircles the horse's head above the nostrils while the nose bar holds the mask in position.

The cover 14 is formed of a thick, open cell, foamed plastic sheet 35 which is shaped to correspond to the frame upon which it secured. In order to form the sheet into the dome-like shape of the frame, the sheet may be formed in separate segments which are appropriately stitched or sealed together along lines 36. Commercially available, open-cell urethane foam, which is used in filters, can be used to form the cover sheet.

In order to retain the pre-determined shape of the cover, as well as to protect it against damage or excess distortion and to support the relatively weak open cell foamed plastic material which makes up the cover, the cover is surrounded by a net cover 35 made of a strong plastic web material, such as nylon netting. For example, the netting can be obtained in cylindrical shape which is stretched over the dome-like shape of the cover and the netting end portion 39 near the crown 40 of the cover may be pulled into the seam or stitching at the lines 36 to thereby secure the netting to the cover.

Figure 8:
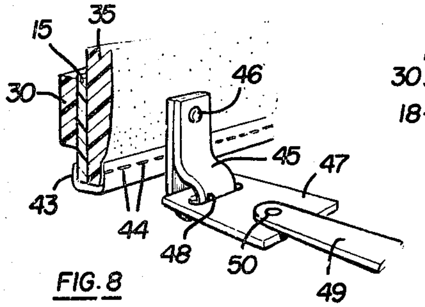
FIG. 8 is a fragmentary, perspective view, of the pivoted tab for fastening a strap to the mask.
Figure 9:
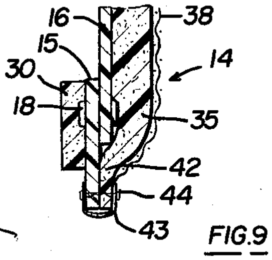
FIG. 9 is an enlarged, cross sectional view, taken in direction of arrows 9—9 of FIG. 6.

The open bottom edge portion 42 of the cover is compressed and finished with a binding strip 43 (see FIGS. 8 and 9) which surrounds the adjacent netting portion and rearward edge of the band 15. The binding strip may be secured to the adjacent cover and band portions by means of a line of stitching 44 or the like.

The binding material may be formed of a flexible plastic sheet which is relatively smooth and easy to clean and is strong enough for the intended purpose. The open cell, thick cover sheet 35 may be made of a suitable foamed polyurethane or the like material which is capable of withstanding the weather and atmospheric conditions as well as the attack from the horse's breathing, mucus and other possible discharges, and from dirt and dust.

In order to secure the mask upon the horse's head, flexible strips double bent into loops 45 are fastened by the rivets 46 to the cover and adjacent band 15 portions. A strap tab 47 is provided with a slot 48 through which the loop 45 passes. An elongated strap 49 is fastened by a rivet 50 to the tab. Thus, the straps may pass lengthwise along, then around the rear of, the horse's head and back to the opposite side of the mask. Thus, by means of the single strap connection, the mask may be applied upon a horse which already has a bridle and bit applied to its head, without interfering with the bridle, bit and rein actions. Because of the loop fitted through the slot in the tab, the tab tends to normally extend outwardly, i.e., radially or transversely relative to the bottom opening in the mask to thereby hold the strap out of the way for easy application of the mask upon the horse's nose. Then, by pulling the strap, the tabs tend to fold into the plane of the side of the horse's face, i.e., into the general plane of the loops for fastening purposes.

The strap 49 may be provided with an appropriate buckle arrangement for shortening or lengthening it. However, this is omitted for illustration purposes.

Figure 10:
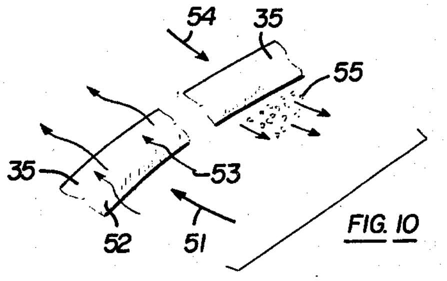
FIG. 10 is a schematic diagram showing the movement of exhaled breath and inhaled fresh air through the mask cover.

In operation, and referring to FIG. 10 which schematically illustrates fragments of the cover sheet 35, the horse breaths through the cover material. That is, when the horse exhales breath, illustrated by the arrow 51, the breath passes outwardly through the wall 35 of the cover 14 (see arrows). As the moisture laden exhaled breath passes through the sheet 35, a portion of the moisture tends to condense within the inner areas of the sheet 35 as shown by the shaded portion 52. Meanwhile, heat is retained within the space 53 above the horse's nostrils due to the insulating effect of the condensation, to retain some of the heat of the expelled breath.

Upon inhaling, the fresh air, illustrated by the arrow 54, passes through the sheet 35 from the outside toward the horse's nostrils, and, pick up some of the moisture 55 which had been earlier condensed within the wall of the cover. This happens particularly on cold, sub-freezing temperature days where the air is normally relatively dry. In addition, the cold air tends to pick up heat from the warmed area 53 before being inhaled. Consequently, there is a breathing cycle that takes place in cold weather which momentarily holds some of the moisture and heat from exhaled breath. Upon inhaling, the moisture is recycled into the cool, fresh, dry air which is also momentarily pre-heated before being inhaled.

As can be seen, the mask tends to act as a filter for dust and dirt during those atmospheric conditions. Alternatively, it acts as a moisture applicator and preheater during cold weather times.

Further, the mask may be used as a vaporizer by applying liquid vaporizer inhalants to the interior pad 21. Then, upon applying the mask to the horse's nose area, the inhalant tends to vaporize so that the horse breathes in this material. Thus, a very simple, inexpensive inhaler or vaporizer is made available utilizing the same mask.

The mask may be easily cleaned by hosing it with a suitable blast of pressurized water. It will rapidly dry because of the open cell, porous nature of the cover and the open frame which tends to easily breath or pass liquid and gas.

Having fully described an operative embodiment of this invention, I now claim:

1. A bag-like mask for fitting over and receiving the forward, i.e., nose and mouth, portion of a horse's head, comprising:

an approximately dome-like shaped frame having a rear open end formed of a ring-like base member through which the forward end of the horse's head is inserted, and having frame members extending forwardly from the base member and joined together to form the closed forward end of the frame, with the frame members being spaced a distance outwardly from the adjacent head portions;

a cover shaped to correspond to the frame shape, and being fitted over and secured to the frame; said cover being formed of a relatively thick wall, flexible, open cell, foamed plastic material, releasable fastening means for securing the mask upon a horse's head for wearing during exercising, as well as when the horse is stationary;

a nose engaging bar arranged within the frame and comprising an elongated, flat, semi-flexible, relatively stiff strip having one end secured to the base member, and its opposite end secured to the frame at the closed forward end thereof, with the bar being bent in between its ends for resting upon the upper surface of the horse's head, at the nose portion, and between the horse's nostrils for thereby positioning and holding the frame upon the horse's head, but with the frame spaced a distance from the horse's nostrils;

an absorbent pad arranged within the mask between the nose bar and the closed forward end of the frame for absorbing and emitting inhalants applied to the pad;

the cover material cell size being sufficiently air pervious to substantially freely pass air therethrough, but to screen a substantial portion of dust and the like carried by the air, and the cover wall being of sufficient thickness to tend to produce a cold weather breathing cycle wherein a part of the moisture in exhaled breath condenses in the wall portion near the inner surface of the cover so that the condensation tends to insulate and help retain some heat within the mask, and wherein fresh air inhaled passes through such condensation and retained heat and tends to pick up some moisture and become somewhat preheated before inhalation thereof.

2. A mask as defined in claim 1, and said releasable fastening means including a flat loop forming strip bent into a loop shape with overlapping ends secured to the frame base member; a tab member having an end with a slot through which the strip loop passes for pivotally connecting the tab to the base member;

and the tab member having an opposite end upon which the end of an elongated flexible strap is secured, with the strap being formed to pass lengthwise along and around the rear of the horse's head and with the opposite end of the strap being secured to the base member at a location oppositely to the location where the loop forming strip is secured.

3. A mask as defined in claim 1, and including a flat loop forming strip bent into a loop shape with its overlapping ends secured to the frame base member;

a tab member having an end with a slot through which the loop passes for pivotally connecting the tab to the base member, with the tab normally extending radially outwardly relative to the base member, but being pivotable into longitudinal alignment with the mask;

an elongated flexible strap secured to the tab member, with the strap being arranged to pass lengthwise along the horse's head for engagement therewith, and with the opposite end of the strap being secured to the base member at a location oppositely to the location of the loop forming strip.

4. A mask as defined in claim 1, and said frame base member being formed of a substantially flat, thin strip of semi-flexible, i.e., relatively stiff, but somewhat resiliently flexible, material which normally holds its shape, but may be bent out of shape and will resiliently return to its previous shape, with said strip being bent into a ring-like band for encircling the adjacent portion of the horse's head;

and said frame members being formed of similar strips, each connected at one end to said band and each extending forwardly to where its opposite ends are joined to the other strip ends, with the frame member strips being bent between their ends to form a dome-like shape which generally conforms to the external configuration of the forward portion of a horse's head.

5. A mask as defined in claim 4, and including padding attached upon the internal surface of said band for resting upon the surface of the adjacent portion of the horse's head, while the frame is otherwise spaced away from the adjacent surfaces of the horse's head.

6. A mask as defined in claim 4, and including a stretch resistent net, having relatively wide openings, arranged upon and covering the outer surface of the cover and secured to the cover near the open rear end thereof, said net being sufficiently flexible, so as to flex and move with the cover and frame, but reinforcing and holding the cover against stretching and distortion.

* * * * *